United States Patent [19]

Robinson et al.

[11] Patent Number: 4,511,749

[45] Date of Patent: Apr. 16, 1985

[54] CONVERSION OF METHANOL TO TOLUENE USING AMORPHOUS SILICA-ALUMINA CATALYSTS

[75] Inventors: Joseph G. Robinson, Winchcombe; Pierce W. F. Riemer, Huntly, both of England

[73] Assignee: Coal Industry Patents Limited, London, England

[21] Appl. No.: 554,244

[22] Filed: Nov. 22, 1983

[30] Foreign Application Priority Data

Feb. 11, 1983 [GB] United Kingdom ............... 8303772

[51] Int. Cl.³ ............................................. C07C 1/20
[52] U.S. Cl. ....................................... 585/469; 585/640
[58] Field of Search ............... 585/469, 640; 502/177, 502/240, 258, 260

[56] References Cited

U.S. PATENT DOCUMENTS

| | | | |
|---|---|---|---|
| 2,519,622 | 8/1950 | Archibald et al. | 502/263 |
| 3,457,191 | 7/1969 | Erickson et al. | 502/263 |
| 3,634,332 | 1/1972 | Bambrick | 502/263 |
| 3,652,216 | 3/1972 | Krekeler et al. | 502/330 |
| 3,969,274 | 7/1976 | Frampton | 502/258 |
| 3,970,588 | 7/1976 | Taylor et al. | 502/258 |
| 4,060,568 | 11/1977 | Rodewald | 585/469 |
| 4,079,095 | 3/1978 | Givens et al. | 585/640 |
| 4,197,418 | 4/1980 | Lee et al. | 585/469 |
| 4,238,631 | 12/1980 | Daviduk et al. | 585/469 |
| 4,427,578 | 1/1984 | Robinson et al. | 502/177 |

FOREIGN PATENT DOCUMENTS

WO82/0018-66  6/1982  PCT Int'l Appl. ............... 585/640

*Primary Examiner*—Delbert E. Gantz
*Assistant Examiner*—Cynthia A. Prezlock
*Attorney, Agent, or Firm*—Stevens, Davis, Miller & Mosher

[57] ABSTRACT

Amorphous silica-alumina catalysts, having a layer of an aluminum compound chemically bonded onto the surface of a silica xerogel and having protons as the electrical charge balancing species, have been found to give surprising selectivity in the conversion of water/methanol mixtures to toluene.

7 Claims, No Drawings

CONVERSION OF METHANOL TO TOLUENE USING AMORPHOUS SILICA-ALUMINA CATALYSTS

This invention concerns a catalytic process, more especially it concerns the catalytic conversion of an alcohol to an aromatic hydrocarbon.

Our co-pending U.S. patent application, No. 554,246, discloses a novel silica-alumina catalyst which comprises a highly porous amorphous silica xerogel having a layer of an aluminum compound chemically bonded onto up to 90% of the available area of the silica surface, the catalyst having a maximum pore diameter of about 1.1 nm and having substantially only protons and/or transition metal cations as electrical charge balancing species on the surface of the layer. Assignee's co-pending application also describes a method for the preparation of this catalyst using as starting material a highly amorphous silica xerogel material having a layer of aluminum compound chemically bonded onto up to 90% of the available area of the silica surface, for a sample prepared according to assignee's British Published Application No. 2,100,710A. The starting material is treated with an ammonium salt solution capable of exchanging labile cations for ammonium ions, washed with deionized water until no further ammonium cations can be detected, optionally ion exchanged to deposit transition metal cations on the surface, dried and calcined.

We have now discovered an unexpected activity of certain of such catalysts. It is suggested in Bristish patent specification No. 1,589,857 that crystalline zeolite catalysts catalyse the conversion of methanol with added water with selectivity to ethylene and propylene. This was not observed using the amorphous silica-alumina catalysts of our abovementioned co-pending application which yield a range of $C_1$-$C_7$ alkylbenzenes, but certain catalysts exhibited a very high selectivity to toluene.

Accordingly, the present invention provides a process for the production of toluene with high selectivity, comprising passing methanol with at least an equal weight of water over a silica xerogel having a layer of an aluminum compound chemically bonded onto the surface of the silica in an amount equivalent to a monolayer on up to 90% of the BET surface area of the silica, said catalyst having a maximum pore diameter of about 1.1 nm, having substantially only protons as electrical charge balancing species on the surface of the layer, the reaction causing bonding of the layer onto the surface of the silica having been carried out at a temperature of from 300° to 600° C., and the catalyst having been calcined at a temperature not exceeding 600° C., preferably 300° to 450° C., at a process reaction temperature of 280° to 600° C., preferably 300° to 450° C.

The process may be carried out using known forms of catalytic reactors, especially fluidized or fixed bed reactors. Suitable liquid hourly space velocities are in the range 0.1 to 5.0 $h^{-1}$, preferably 0.2 to about 1 $h^{-1}$. The reaction is conveniently carried out at atmospheric pressure but pressures above or below atmospheric may be used.

The temperature of calcination of the catalyst appears to be important, and is preferably less than 450° C., more preferably 300° to 350° C.

The concentration of the water/methanol feedstock is preferably in the region 3:1 to 4:1 by weight.

Under preferred conditions, the selectivity for toluene is in excess of 90%, with an overall conversion of methanol in the 30 to 50% range.

The present invention will now be described by way of example only.

EXAMPLE

A sample (100 g) of commercial silica xerogel was heated in an oven for 4 hours at 120° C. to remove physically absorbed water. The dried xerogel was cooled in a desiccator and immersed in 250 ml of a 33.87% w/v solution of aluminum sec-butoxide in dry hexane, in an amount sufficient to cover 50% of the BET surface with a monolayer of the aluminum alkoxide after removal of the solvent. The pressure was reduced to assist the solvent to enter the pores of the xerogel. After 12 hours the liquor was decanted and the material transferred to a vacuum oven where it was dried.

After soaking in deionized water for 16 hours and drying again in the vacuum oven, the material was heated at 500° C. for 4 hours. A sample of the material was packed into a column and a 0.1M aqueous solution of ammonium nitrate was pumped through the column. Samples of the eluent were tested periodically for the presence of aluminum by the addition of a few drops of 0.1M sodium hydroxide solution; samples containing aluminum cation were characterized by the formation of a gelatinous precipitate. When no further aluminium could be detected in this way, the ammonium nitrate solution was replaced by deionized water and pumping continued until the pH of the eluent was identical with that of the feed water. The product was removed from the column, dried under reduced pressure and thereafter calcined at 325° C. for 4 hours.

Studies of the resulting catalyst showed that it consisted of collections of particles of 2–10 nm diameter having a strongly electron-scattering surface layer which was an integral part of the silica matrix. There was little fine microporosity, but the gaps between particles were approximately 1.0 nm.

Degassed methanol/water mixtures were pumped by a positive displacement pump through a preheater packed with glass beads before the methanol/water vapour was passed into a tubular reactor packed with the catalyst, at a liquid hourly space velocity of 1.0 $h^{-1}$. The tubular reactor was run at various temperatures, 250°, 300° 350°, 400° and 450° C., and the preheater was maintained at 5° C. below the reaction temperature. The products emerging from the reaction tube were collected as a liquid fraction in an ice-cooled trap and a very small gaseous fraction (insufficient for analysis) in a gas reservoir. The products were analyzed and the results are shown in Table 1 below.

TABLE 1

| Water/Methanol wt. ratio 3:1 | | | | | |
|---|---|---|---|---|---|
| Bed temperature (°C.) | 250 | 300 | 350 | 400 | 450 |
| Methanol conversion (wt %) | 3.2 | 47 | 49 | 41 | 27 |
| Cycloalkanes (wt %) | — | 1.1 | 0.8 | 1.2 | 3.1 |
| Toluene (wt %) | — | 93.5 | 95.7 | 92.5 | 90.0 |
| $C_2$ alkyl benzene (wt %) | — | 3.0 | 2.5 | 4.3 | 6.0 |
| $C_3$ alkyl benzene (wt %) | — | 1.5 | 0.9 | 1.9 | 0.9 |

The above-described procedure was repeated, except that the catalyst was calcined at 600° C. for 4 hours, and the results are shown in Table 2 below.

TABLE 2

| Water/Methanol wt. ratio 3:1 | | | | | |
| --- | --- | --- | --- | --- | --- |
| Bed temperature (°C.) | 250 | 300 | 350 | 400 | 450 |
| Methanol conversion (wt %) | 0 | 22 | 32 | 48.1 | 50.2 |
| Cycloalkanes (wt %) | — | 4.7 | 1.5 | 2.6 | 4.6 |
| Toluene (wt %) | — | 42.1 | 41.8 | 32.0 | 15.8 |
| $C_2$ alkyl benzene (wt %) | — | 22.1 | 10.4 | 2.2 | 3.0 |
| $C_3$ alkyl benzene (wt %) | — | 10.1 | 7.8 | 6.1 | 5.2 |
| $C_4$ alkyl benzene (wt %) | — | 7.7 | 10.0 | 17.2 | 19.1 |
| $C_5$ alkyl benzene (wt %) | — | 10.5 | 11.1 | 18.9 | 28.2 |
| $C_6$ alkyl benzene (wt %) | — | 1.2 | 15.3 | 19.8 | 21.1 |
| $C_7$ alkyl benzene (wt %) | — | 1.2 | 2.0 | 1.1 | 3.0 |

It can be seen that though toluene is still a major product, the selectivity has been substantially reduced. The spread of products is broadly similar to that when pure methanol is used as feedstock under the same conditions, instead of water/methanol.

Instead of 3:1 water/methanol, a 1:2 water/methanol mixture was used, using the catalyst calcined at 600° C. The results are shown in Table 3 below, from which it can be seen that there is no selectivity for toluene.

TABLE 3

| Water/Methanol wt. ratio 1:2 | | | | | | |
| --- | --- | --- | --- | --- | --- | --- |
| Bed Temperature (°C.) | 200 | 250 | 200 | 350 | 400 | 450 |
| Methanol conversion (wt %) | 2.6 | 10.7 | 25.4 | 38.2 | 49.8 | 60.1 |
| Cycloalkanes (wt %) | 4.0 | 1.0 | 0.3 | 1.6 | 2.6 | 3.9 |
| Toluene (wt %) | 9.5 | 11.1 | 11.0 | 8.2 | 6.9 | 9.9 |
| $C_2$ alkyl benzene (wt %) | 16.5 | 16.2 | 14.8 | 13.7 | 10.8 | 12.0 |
| $C_3$ alkyl benzene (wt %) | 19.7 | 20.9 | 19.7 | 17.2 | 16.1 | 14.8 |
| $C_4$ alkyl benzene (wt %) | 22.0 | 19.7 | 18.1 | 17.0 | 17.0 | 16.9 |
| $C_5$ alkyl benzene (wt %) | 21.0 | 21.6 | 19.8 | 23.2 | 26.8 | 22.1 |
| $C_6$ alkyl benzene (wt %) | 4.9 | 8.2 | 15.2 | 17.9 | 19.7 | 18.2 |
| $C_7$ alkyl benzene (wt %) | 2.4 | 1.3 | 1.1 | 1.2 | 1.2 | 2.3 |

Further tests using a pure methanol feedstock and using the catalyst calcined at 600° C. showed a range of alkyl benzenes produced.

We claim:

1. A process for the production of toluene with high selectivity, comprising passing methanol with at least an equal weight of water over a silica-alumina catalyst which comprises a highly porous amorphous silica xerogel having a layer of an aluminum compound chemically bonded onto the surface in an amount equivalent to a monolayer on up to 90% of the BET surface area of the silica xerogel, said catalyst having a maximum pore diameter of about 1.1 nm, having substantially only protons as electrical charge balancing species on the surface of the layer, the reaction causing bonding of the layer having been carried out at a temperature of from 300° to 600° C. and the catalyst having been calcined at a temperature not exceeding 600° C., at a process reaction temperature in the range 280° to 600° C.

2. A process as claimed in claim 1, wherein the process reaction temperature is in the range 300° to 450° C.

3. A process as claimed in claim 1, wherein the concentration of the water/methanol feedstock is in the range 3:1 to 4:1 by weight.

4. A process as claimed in claim 1, wherein the liquid hourly space velocity is in the range 0.1 to 5.0 h$^{-1}$.

5. A process as claimed in claim 4, wherein the liquid hourly space velocity is in the range 0.2 to about 1 h$^{-1}$.

6. A process as claimed in claim 1, wherein the catalyst has been calcined at a temperature not exceeding 450° C.

7. A process as claimed in claim 1, wherein the calcination temperature is in the range 300° to 350° C.

* * * * *